United States Patent [19]

Meilland

[11] Patent Number: Plant 7,376

[45] Date of Patent: Nov. 6, 1990

[54] ROSE PLANT—MEIVOUPLIX VARIETY

[75] Inventor: Alain A. Meilland, Antibes, France

[73] Assignee: The Conard-Pyle Company, West Grove, Pa.

[21] Appl. No.: 406,542

[22] Filed: Sep. 13, 1989

[30] Foreign Application Priority Data

Sep. 19, 1988 [FR] France ..... 7991

[51] Int. Cl.[5] ..... A01H 5/00

[52] U.S. Cl. ..... Plt./15

[58] Field of Search ..... Plt./15

*Primary Examiner*—James R. Feyrer

*Attorney, Agent, or Firm*—Burns, Doane, Swecker & Mathis

[57] ABSTRACT

A new and distinct variety of Hybrid Tea rose plant is provided which abundantly forms attractive fully double lemon yellow blossoms. Such blossoms are long lasting. The plant exhibits an erect growth habit, vigorous vegetation, and is well suited for greenhouse forcing for cut flower production. Additionally, the plant exhibits excellent disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Dr. Verhage variety (nonpatented in the United States). The male parent (i.e., the pollen parent) was the Meitakilor variety (nonpatented in the United States). The parentage of the new variety can be summarized as follows:

[Dr. Verhage variety × Meitakilor variety].

The seeds resulting from the above pollination were sown and small plants were obtained which were physically and biololgically different from each other. Selective study resulted in the identification of a single plant of the new variety.

It was found that the new variety of Hybrid Tea rose plant of the present invention possesses the following combination of characteristics:

(a) forms in abundance attractive long lasting fully double lemon yellow blossoms,
(b) exhibits an erect growth habit,
(c) is well adapted for greenhouse forcing,
(d) exhibits vigorous vegetation,
(e) is particularly suited for cut flower production, and
(f) exhibits excellent disease resistance.

The blossom coloration is fairly well maintained during the vase life of the cut flowers.

The new variety well meets the needs of the horticultural industry for all uses and is particularly well suited for cut flower production.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meivouplix variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indicia* undertook and growing in greenhouses at Cap d'Antibes, France.

DETAILED DESCRIPTION

Figures 1, 2, 3, 4, 5, 6, 7, 8, 9, 10, 11, 12, 13, 14, 15, 16:
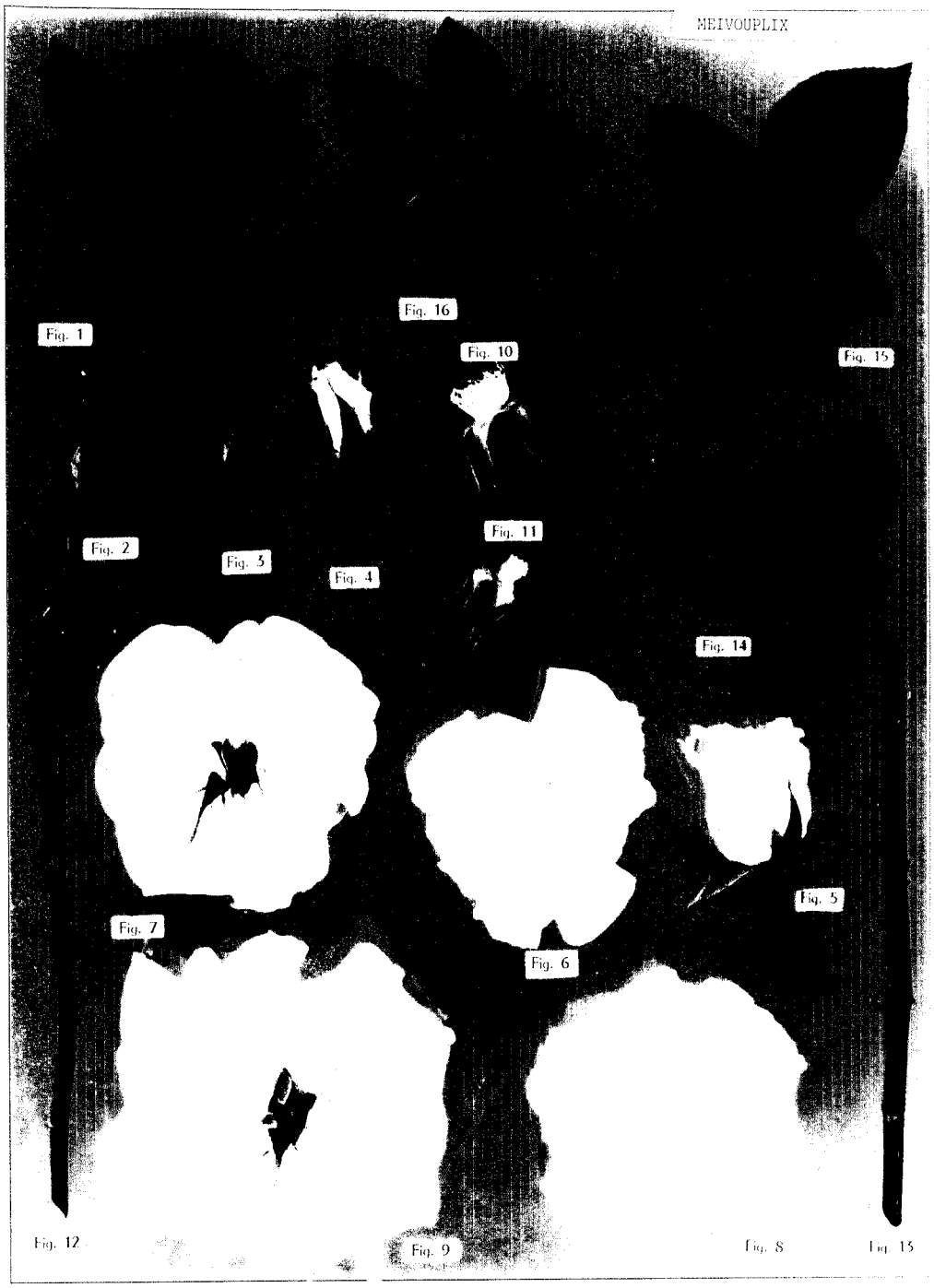
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch shown upside down.
FIG. 14 illustrates a specimen of a leaf with three leaflets — plan view — upper surface.
FIG. 15 illustrates a specimen of a leaf with seven leaflets — plan view — upper surface.
FIG. 16 illustrates a specimen of a leaf with five leaflets — plan view — under surface.

The chart used in the identification of the colors is that of The Royal Horticultural Society (R.H.S. Colour Chart). The description is based on the observation of two year old plants made during November while budded on *Rosa indicia* understock and growing in greenhouses at Cap d'Antibes, France. The coloration in common terms precedes reference to the chart.

Class: Hybrid Tea.

Plant:

*Height.*—Plants which were pruned to a height of 85 cm. produce floral stems having a length of approximately 40 to 70 cm.

*Habit.*—Erect.

Branches:

*Color.*—Young stems: lettuce green, Yellow-Green Group 144A, more or less stained with reddish brown. Adult wood: medium green, Yellow-Green Group 146B.

*Thorns.*—Size: average. Quantity: very few. Color: greenish on young stems and greenish changing to tan mature wood.

Leaves:

*Stipules.*—Adnate, pectinate, very wide and linear.

*Petioles.*—Upper surface: striped reddish brown on young foliage and medium green on adult foliage with more or less glandular edges. Under surface: light green, bear a few prickles.

*Leaflets.*—Number: 3, 5, and 7 (most often). Sometimes the first pair of leaves is incompletely formed. Shape: oval. Serration: single and regular. Texture: consistent. General appearance: bright and dense foliage. Color (young foliage): Upper surface: lettuce green, Yellow-Green Group 144A, very widely stained with reddish brown. Under surface: lettuce green, Yellow-Green Group144A, very widely stained with reddish brown. Color (adult foliage): Upper surface: dark green, Green Group 137A. Under surface: light green, Green Group 137D.

Inflorescence:

*Number of flowers.*—Generally one per stem.

*Peduncle.*—Very long, straight, rigid, smooth, light green in coloration. The length is approximately 9 to 11 cm. on average.

*Sepals.*—Upper surface: tomentose, greenish in coloration. Under surface: medium green in coloration, the edges of the outer sepals are more or less glandular and only slightly appendiculated.

*Buds.*—Shape: conical and elongated. Length: approximately 3 to 3.5 cm. on average. Size: large. Color upon opening: Upper surface: dark lemon yellow, Yellow-Orange Group 14A. Under surface: lemon yellow, Yellow-Orange Group 14B.

*Flower.*—Shaped: cup-like and very double. Diameter: approximately 13 to 14 cm. on average. Color (when opening begins): Upper surface: lemon yellow, Yellow Group 13A. Under surface: lemon yellow, Yellow Group 13B. Color (when blooming): Upper surface: lemon yellow, Yellow Group 13A. lighter on the edges of the petals and turning somewhat whitish on the outer petals. Under surface: lemon yellow, Yellow Group 13A, lighter on the edges of the petals and turning somewhat whitish on the outer petals. Color (at end of opening): Upper surface: lemon yellow, Yellow Group 13A, lighter on the edges of the petals and turning somewhat whitish on the outer petals. Under surface: lemon yellow, Yellow Group 13A, lighter on the edges of the petals and turning somewhat whitish on the outer petals. Fragrance: slight. Lasting quality: long. Petal number: approximately 40 on average. Texture: consistent. Petal drop: good. Stamen number: aproximately 168 to 178 on average. Anthers: bright yellow edged with ochre. Filaments: normal, saffron yellow in coloration, of irregular heights. Pistils: approximately 131 to 142 on average. Stigmas: normal, ochre in coloration. Styles: greenish, more or less twisted, of irregular heights. Receptacle: smooth, light green, in longitudinal section it is in the shape of a wide pitcher.

Development:

*Vegetation.*—Vigorous.

*Blooming.*—Very abundant.

*Resistsnce to diseases.*—Very good.

*Aptitude to forcing.*—Excellent.

I claim:

1. A new and distinct variety of Hybrid Tea rose plant characterized by the following combination of characteristics:

(a) forms in abundance attractive long lasting fully double lemon yellow blossoms, (b) exhibits an erect growth habit, (c) is well adapted for greenhouse forcing, (d) exhibits vigorous vegetation, (e) is particularly suited for cut flower production, and (f) exhibits excellent disease resistance:

substantially as herein shown and described.

* * * * *

MEIVOUPLIX